US008747791B2

(12) United States Patent
Kawazu

(10) Patent No.: US 8,747,791 B2
(45) Date of Patent: Jun. 10, 2014

(54) CALCIUM PHOSPHATE POROUS MATERIAL WITH SMALL AMOUNT OF REMAINING AROMATIC HYDROCARBON

(75) Inventor: Hideyuki Kawazu, Tokyo (JP)

(73) Assignee: Catalymedic Inc., Funabashi-Shi, Chiba (CN)

( * ) Notice: Subject to any disclaimer, the term of this patent is extended or adjusted under 35 U.S.C. 154(b) by 664 days.

(21) Appl. No.: 12/616,977

(22) Filed: Nov. 12, 2009

(65) Prior Publication Data

US 2010/0119430 A1    May 13, 2010

(30) Foreign Application Priority Data

Nov. 13, 2008 (JP) ................. 2008-313719
Apr. 15, 2009 (JP) ................. 2009-099342

(51) Int. Cl.
*C01B 15/16* (2006.01)
(52) U.S. Cl.
USPC ........................................... 423/311
(58) Field of Classification Search
USPC ........................................... 423/311
See application file for complete search history.

(56) References Cited

U.S. PATENT DOCUMENTS

| 2004/0064194 | A1* | 4/2004 | Irie et al. ............... 623/23.61 |
| 2005/0031704 | A1* | 2/2005 | Ahn ............................ 424/602 |
| 2005/0049717 | A1* | 3/2005 | McGowan ............... 623/23.56 |
| 2010/0112330 | A1  | 5/2010 | Kuwayama et al. |

FOREIGN PATENT DOCUMENTS

| EP | 705802 A1 * | 4/1996 |
| EP | 1 380 313 | 1/2004 |
| JP | 63-40782 | 2/1988 |
| JP | 01-108143 | 4/1989 |
| JP | 3-69844 B2 | 11/1991 |
| JP | 5237178 A | 9/1993 |
| JP | 2597355 B2 | 1/1997 |
| JP | 2001-224679 | 8/2001 |
| JP | 3262233 B2 | 3/2002 |
| JP | 2003-507132 | 2/2003 |
| JP | 2003199815 A * | 7/2003 |
| JP | 2004-33772 | 2/2004 |
| JP | 2004262758 A | 9/2004 |
| JP | 2004284898 A | 10/2004 |
| JP | 2005154373 A | 6/2005 |
| JP | 2007290952 A | 11/2007 |
| WO | 01/13970 | 3/2001 |
| WO | 01/44141 | 6/2001 |

(Continued)

OTHER PUBLICATIONS

Toriyama et al., "Synthesis of β-Tricalcium Phosphate by Use of Wet Milling", Yogyo Kyokai-shi, 1986, pp. 78-82.

(Continued)

*Primary Examiner* — Melissa Stalder
(74) *Attorney, Agent, or Firm* — Ping Wang; Andrews Kurth LLP

(57) ABSTRACT

The purpose of the present invention is to provide calcium phosphate porous material with small amount of the remaining polycyclic aromatic hydrocarbons that are toxic substances. The present invention relates to a method for the production of calcium phosphate porous material of β-tricalcium phosphate comprising calcining micronized β-tricalcium phosphate wherein a temperature in a furnace is retained at a temperature in a range of 250-550° C. for a certain period of time, or wherein a temperature-rising rate in the furnace while in said range is decreased to one thirds or less of that during ranges before or after said range in said calcining step.

6 Claims, 8 Drawing Sheets

(56) References Cited

FOREIGN PATENT DOCUMENTS

WO    2008/111432    9/2008

OTHER PUBLICATIONS

Kondoh, I. et al., "Sintering of Tricalcium Phosphate by HIP", Journal of the Ceramic Society of Japan, 1989, vol. 97, No. 9, pp. 965-967. (English Abstract only).

Ok, J et al., "In vivo characterization of porous β-TCP with bimodal pore size distribution", Preprints of 17th Fall Meeting of the Ceramic Society of Japan, 2004, p. 144. (English Abstract only).

Kankawa, Y. et al., Injection Molding of β-TCP Powder, Journal of the Ceramic Society of Japan, 1992, vol. 100, No. 2, pp. 211-214. (English Abstract only).

Experiment report by Taihei Chemical Industrial Co., Ltd.

\* cited by examiner

CALCIUM PHOSPHATE POROUS MATERIAL WITH SMALL AMOUNT OF REMAINING AROMATIC HYDROCARBON

FIELD

The present invention relates to calcium phosphate porous material, which is used, for example, for an artificial bone that is transplanted and buried in a living body; prosthetic bone material; separation of a biochemical substance from microorganisms; a carrier for cell culture; and an agent for purification and adsorption, especially to β-tricalcium phosphate porous material with little amount of remaining aromatic hydrocarbon.

BACKGROUND

One of the representative examples of the conventional method for the production of calcium phosphate porous material comprises adding and mixing an aqueous solution of a deflocculant (foaming stabilizer) with micronized calcium phosphate, adding a surfactant (foaming agent) into the resulting mixture to prepare porous fluid having communicated fine pores, subjecting to the porous fluid to a drying treatment to give porous forming material with calcium phosphate structure, calcining the resulting forming material by constantly heating it up to a temperature of 1,000° C. or more at a temperature-rising rate of about 300° C. per hour by means of an electric furnace and the like so as to decompose and vanish said defloccculant and surfactant while sintering it as ceramic (Patent Document 1). This method is depicted in FIG. 1.

Another example of the conventional method for the production of calcium phosphate porous material comprises a step of crushing granule premix consisting of wax binder and micronized calcium phosphate ceramic into granule material with a predetermined diameter, a step of mixing and dispersing said granule material in aqueous foaming slurry consisting of micronized calcium phosphate ceramic, and a step of casting the resulting mixture into a mold with a predetermined shape and a step of drying and calcining the mixture to give prosthetic bone material (Patent Document 2).

Micronized calcium phosphate are known hydroxyapatite and β-tricalcium phosphate. An artificial bone made of hydroxyapatite will bind to bone and have a sufficient initial strength, but is not absorbent. On the other hand, an artificial bone made of β-tricalcium phosphate is absorbent so that it can substitute autologous bone. A method for the mechanochemical production of such micronized calcium phosphate is disclosed, for example, in Patent Documents 3 and 4, and Non-Patent Document 1.

According to the conventional heating and calcining disclosed in the above documents, additives such as the deflocculant, surfactant and/or binders could not be sufficiently decomposed and vanished. Therefore, polycyclic aromatic hydrocarbons would be generated from carbon atoms contained in said additives and remain in such an amount as would affect a living body.

The term "polycyclic aromatic hydrocarbons" is a generic one that means compounds generated due to incomplete combustion during burning of material, some of which are known as showing strong cancer-causing or promoting properties.

In the prior method disclosed in Patent Documents 1 and 2, the calcining or sintering step was performed by heating up to a predetermined temperature (for example, at 1,000~1,300° C.) with a constant temperature-rising rate (for example, 300° C. per hour) and keeping at the predetermined temperature for a certain period of time, or just by heating at a predetermined temperature for a certain period of time. Nothing is described in the above prior art with respect to an amount of the remaining polycyclic aromatic hydrocarbons in the produced calcium phosphate porous material.

[Patent Document 1] Japanese Patent No. 2597355
[Patent Document 2] Japanese Patent Laid-Open Application No. 1993-237178
[Patent Document 3] Japanese Patent No. 3262233
[Patent Document 4] Japanese Patent Publication No. 1991-69844
[Non-Patent Document 1] Motohiro TORIYAMA and Sukezo KAWAMURA, Synthesis of β-Tricalcium Phosphate by use of Wet Milling, Yogyo-Kyokai-shi, 94, 78-82, 1986

DETAILED DESCRIPTION

Figure 1:
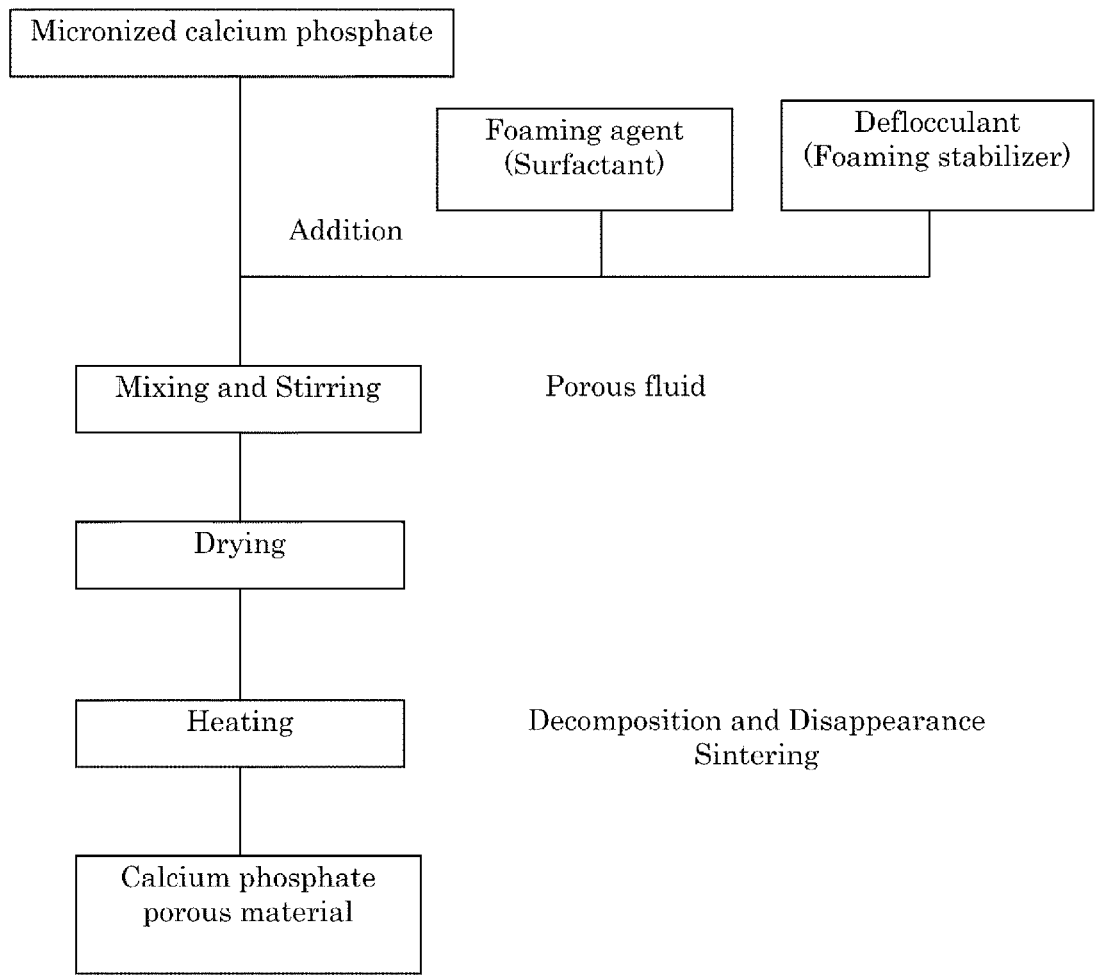
FIG. 1 shows the production process of the calcium phosphate porous material.

Problems to be Solved by the Present Application

It has been strongly desired that an amount of the remaining polycyclic aromatic hydrocarbons should be reduced as much as possible in β-tricalcium phosphate porous material, which is absorbent and may be applied in a living body as the artificial bone.

Means to Solve the Problems

The present inventor examined the process for the production of calcium phosphate porous material by calcining the micronized calcium phosphate by means of thermal analysis. According to the analysis, it was revealed that it was possible to decompose and vanish the polycyclic aromatic hydrocarbons generated from additives such as the deflocculant, surfactant and/or binders with a sufficient amount of thermal energy provided by retaining a temperature for a certain period of time, or decreasing a temperature-rising rate in a range of about 250-550° C. during a calcining or sintering step. As a result, an amount of total organic carbon ("TOC") could be reduced. The present invention has been completed based on the above findings.

Thus, the present invention relates to the following aspects:

[1] Calcium phosphate porous material made of β-tricalcium phosphate having a concentration of total organic carbon of 5 mg/L or less.

[2] A method for the production of calcium phosphate porous material made of β-tricalcium phosphate comprising calcining micronized β-tricalcium phosphate in a furnace, wherein a temperature in a furnace is retained at a temperature in a range of 250-550° C. for a certain period of time, or wherein a temperature-rising rate in the furnace in said range is decreased to one thirds or less of that range above or below said range in said calcining step.

A method for the production of a porous material, comprising; mixing micronized β-tricalcium phosphate with an aqueous solution of a deflocculant;

a foaming agent to form a porous fluid; drying the porous fluid;

calcining the dried porous fluid in a furnace by (1) heating the furnace to a first temperature at a first temperature-rising rate of 50-500° C./hr and maintaining the temperature at the first temperature for a first time period, wherein the first temperature is in the range of 250-550° C.; and (2) heating the furnace from the first temperature to a second temperature at a second temperature-rising rate of 300° C./hr and maintaining the temperature at the second temperature for a second time period, wherein the second temperature is in the range of 1000-1300° C.

An artificial bone or prosthetic bone material comprising the calcium phosphate porous material according to the present invention or the calcium phosphate porous material produced by the method according to the present invention.

Advantages

While the concentration of the total organic carbon in the prior calcium phosphate porous material made of β-tricalcium phosphate is about 30 mg/L or more, that in the prior calcium phosphate porous material according to the present invention is 5 mg/L or less. Thus, as the calcium phosphate porous material according to the present invention has a significantly reduced amount of the remaining polycyclic aromatic hydrocarbons, some of which are cancer-causing compounds, it shows very excellent properties as materials that are applied in a living body such as the artificial bone. As the additives such as the deflocculant, surfactant and/or binders are significantly decomposed and vanished in the calcining step of the method according to the present invention, the amount of the remaining polycyclic aromatic hydrocarbons in the resulting calcium phosphate porous material can be reduced to a significantly low level. Furthermore, osteogenesis will occur more advantageously with use of the prosthetic bone material made of the calcium phosphate porous material according to the present invention.

BEST MODE FOR CARRYING OUT THE PRESENT INVENTION

Calcium phosphate porous material made of β-tricalcium phosphate ($Ca_3(PO_4)_2$) according to the present invention is characterized in that the concentration of total organic carbon ("TOC") is 5 mg/L or less, preferably 4.5 mg/L or less, more preferably 1.9 mg/L or less. The calcium phosphate porous material according to the present invention is porous material with porosity of about 75% and having macro pores with a diameter of 100-400 μm and micro pores with a diameter of a few μm.

Since there are many types of the polycyclic aromatic hydrocarbons, it is known that it would be very difficult to examine a content of each polycyclic aromatic hydrocarbon and access the results. Accordingly, the concentration of the TOC in the calcium phosphate porous material is determined as a value correlating with an amount of the remaining polycyclic aromatic hydrocarbons and used as an index of the same.

The "TOC" in the present specification is defined in accordance with "the Japanese Industrial Standards (JIS) K0102 22. Organic Carbon." The concentration of the TOC is determined according to "JIS K0102 22.1 Combustion-Oxidization—Infrared TOC Analysis." Specifically, calcium phosphate porous material is micronized to powder sample with a diameter of 30 μm or less by means of a mortar and the like. The resulting powder sample is mixed with pure water of water quality criteria A4 according to JIS K0577 at a ratio of 1 (solid):10 (liquid) to give a solution. The resulting solution is then subjected to ultrasonic bath for 30 min. in order to elute its components, followed by centrifugation at 3,000 rpm for 20 min. The resulting supernatant is filtered through a microfilter with 0.45 μm, and the resulting filtrate is used as a sample for the determination by the above Infrared TOC Analysis.

A preferred method for the production of calcium phosphate porous material made of β-tricalcium phosphate according to the present invention comprises calcining micronized β-tricalcium phosphate wherein a temperature in a furnace is retained at a certain temperature in a range of 250-550° C., preferably in a range of 300-500° C. for a certain period of time, for example, for about 2-4 hours, or wherein a temperature-rising rate in the furnace in a range of 250-550° C., preferably in a range of 250-400° C. is decreased to one thirds or less of that in ranges before or after said range, for example, to about 50-100° C./hr. Thus, the method according to the present invention is characterized in the calcining step during the production of the calcium phosphate porous material (FIG. 1).

Specific examples of the method according to the present invention comprise the next steps:
- a step of mixing the micronized β-tricalcium phosphate with an aqueous solution of a deflocculant;
- a step of adding a foaming agent into the resulting mixture to prepare porous fluid having communicated fine pores:
- a step of subjecting the porous fluid to a drying treatment to give dry porous forming material with calcium phosphate structure; and a step of heating the resulting forming material to decompose and vanish the defloculant and foaming agent, and sintering it with heating up to a temperature of 1,000° C. or more.

Thus, the other steps than the calcining step may be carried out in a manner similar to those of the prior art. For example, a normal temperature-rising rate in the calcining step is about 200-400° C./hr, and the temperature may be finally increased to about 1,000-1,300° C.

The micronized β-tricalcium phosphate is a known compound and may be any commercially available one.

The defloculant may be any material known to those skilled in the art, for example, water-soluble high-molecular compounds such as a high-molecular surfactant of polycarboxylic acid-type.

The foaming agent may be any material known to those skilled in the art, including non-ionic surfactant such as polyoxyethylene alkylether, polyoxyethylene nonylphenylether, fatty acid sorbitan ester, alkylpolyglycoside, fatty acid diethanolamide, and alkylmonoglycerylether; or ethylene oxide additives thereof. By using the non-ionic surfactant, adjacent pores will be broken so as to generate communicated pores.

The binder may be any material known to those skilled in the art, including paraffin wax, polyvinyl alcohol, methylcellulose, acryl resin and agarose.

The calcium phosphate porous material produced by the method according to the present invention may be used as a main component of the artificial bone or prosthetic bone material. The artificial bone is classified into a general type and a specific type. The general type includes granular material, porous material (block body, cylindrical body) and shaped type. The specific type may be formed into a variety of shapes depending on its application site, including that for an artificial auditory ossicle, craniotomy trepanation, fixing of petrosa, and pelvis. The calcium phosphate porous material according to the present invention may be preferably used for the general type.

The present invention will be specifically explained below with reference to the examples, which should not be construed to limit the scope of the present invention. The contents of the prior art referred to in this specification are considered to be incorporated as a whole as a part of the disclosure of the present specification.

REFERENCE EXAMPLE

Figure 2:
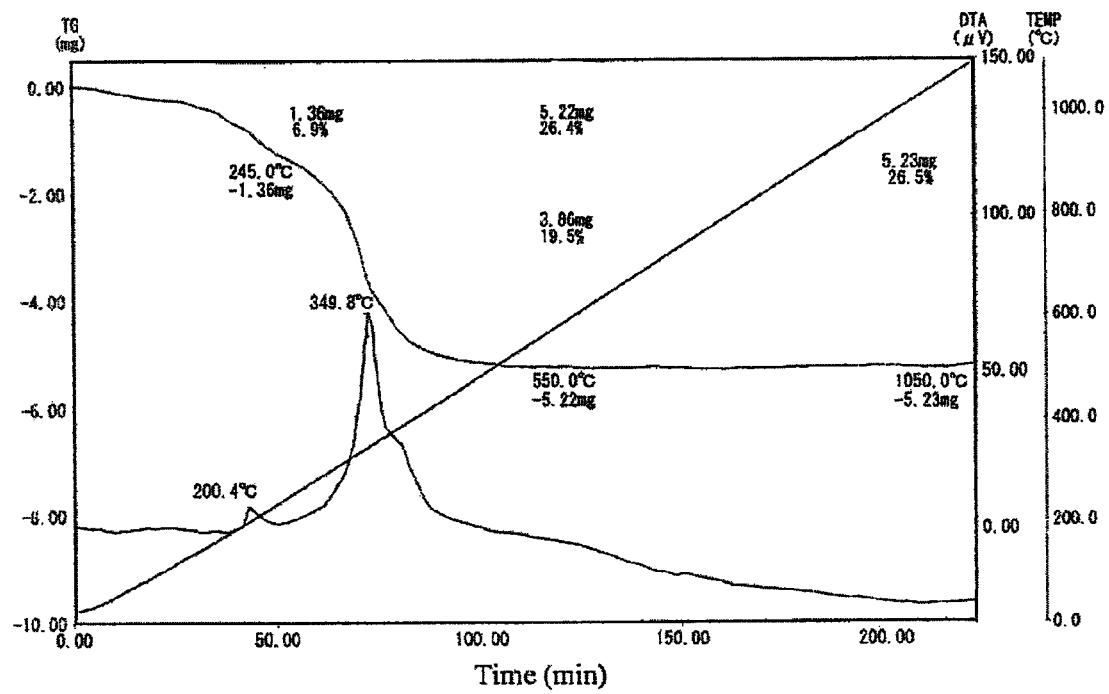
FIG. 2 shows the results of thermal analysis of calcium phosphate porous material before sintering.
Explanation above the figure:
Air: 200 ml/min., Date: 2008 Aug. 6 13:33,
Cell: Aluminum, Temperature-rising rate: 5.0 deg/min.,
Sampling: 0.5 sec,
Weight of the sample: 19.77 mg.

Porous fluid was prepared by mixing the micronized β-tricalcium phosphate with a defloculant (ammonium salt of polycarboxylic acid) and then with a foaming agent (polyoxyethylene alkylether) followed by a drying treatment. The resulting dry porous fluid was then subjected to thermal analysis in accordance with a conventional method to detect the decrease in weight due to decomposition and disappearance. As shown by the results in FIG. 2, the decrease of weight began at a temperature in a furnace of about 200° C. and almost completed at about 550° C. A few peak values in thermal analysis were observed between these temperatures. This data demonstrated that almost all of the defloculant and the foaming agent were decomposed and vanished by the heat treatment in a range of about 250-550° C. Accordingly, it was suggested that the TOC value can be reduced by retaining a temperature for a certain period of time, or decreasing a temperature-rising rate in the above range during the calcining or sintering step so as to provide a sufficient amount of thermal energy.

Example 1

Figure 4:
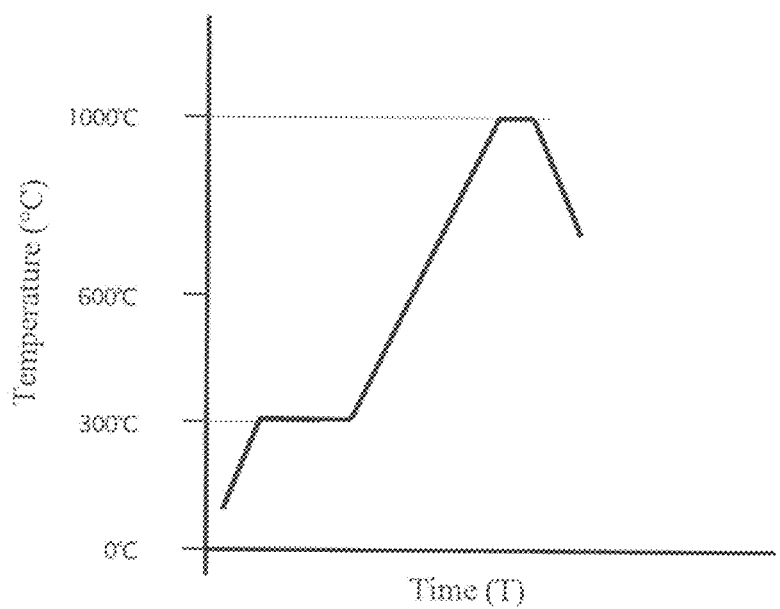
FIG. 4 is the heating and calcining (sintering) pattern according to Example 1. A vertical axis shows a calcining temperature (° C.) in a furnace and an abscissa axis shows time (hour).

The micronized β-tricalcium phosphate (10 g) with a diameter of 0.3 μm or less was mixed with 10 cc of a defloculant (10% ammonium salt of polyacrylic acid). The resulting mixture was then mixed with 1.8 g of a foaming agent (polyoxyethylene nonylphenylether) and stirred with a stirrer to uniformly foam. The resulting porous fluid was poured into a vessel having a particular shape with paraffin paper lining, which was then placed in an incubator to be kept at 40° C. for 20 hours for drying. After drying, it was transferred to an aluminum vessel for sintering by being heated up to 300° C. at a temperature-rising rate of 300° C./hr, retained at 300° C. for 4 hours, then heated up to 1,000° C. at a temperature-rising rate of 300° C./hr, and retained at 1,000° C. for 40 min (FIG. 4).

Figure 3:
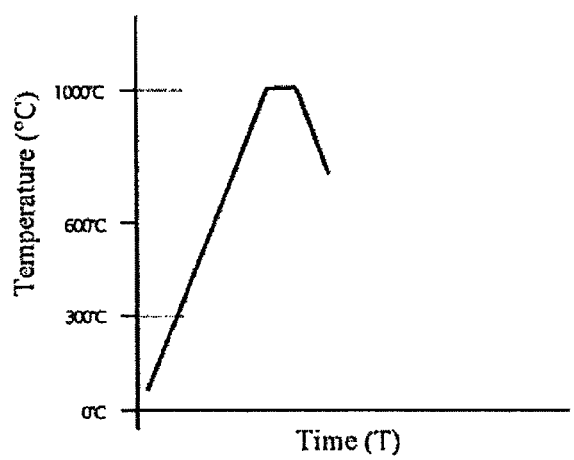
FIG. 3 is the heating and calcining (sintering) pattern according to the prior art. A vertical axis shows a calcining temperature (° C.) in a furnace and an abscissa axis shows time (hour).

The sintered product prepared in Example 1 showed the concentration of TOC of 4.3 mg/L, which correlates with an amount of the polycyclic aromatic hydrocarbons, and electric conductivity of 3.97 mS/m. Said product had communicated pores with a pore size of about 0.2-0.8 mm. The X-ray analysis showed that the product had the same crystal structure of β-tricalcium phosphate as that of the starting material. On the other hand, the porous calcium phosphate material prepared in accordance with the prior method that did not comprise retention at 300° C. for 4 hours (FIG. 3) showed the concentration of TOC of 30.0 mg/L and electric conductivity of 8.50 mS/m. The electric conductivity was determined in accordance with "JIS K0102 13."

Example 2

Figure 5:
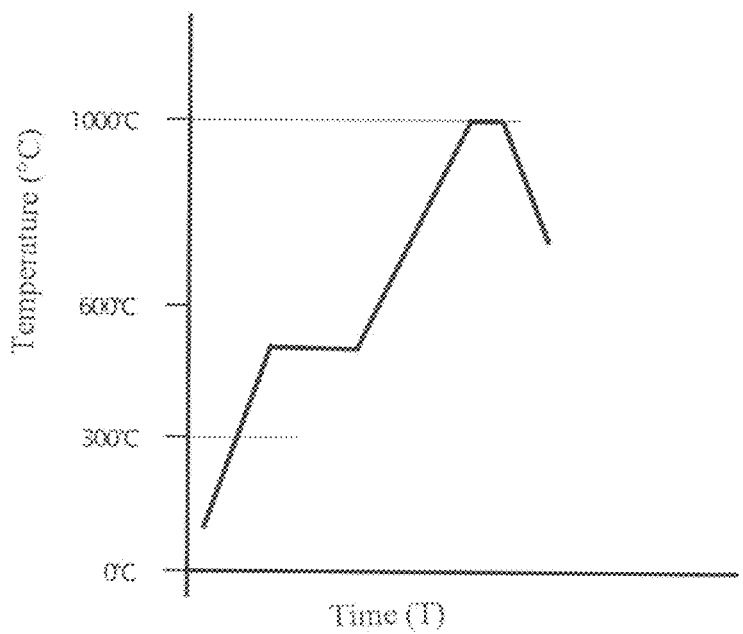
FIG. 5 is the heating and calcining (sintering) pattern according to Example 2. A vertical axis shows a calcining temperature (° C.) in a furnace and an abscissa axis shows time (hour).

The micronized hydroxyappatite (10 g) with a diameter of 0.3 μm or less was mixed with 10 cc of a defloculant (20% ammonium salt of polyacrylic acid). The resulting mixture was then mixed with 1.8 g of a foaming agent (polyoxyethylene nonylphenylether) and stirred with a stirrer to uniformly foam. The resulting porous fluid was poured into a vessel having a particular shape with paraffin paper lining, which was then placed in an incubator to be kept at 50° C. for 24 hours for drying. After drying, it was transferred to an aluminum vessel for sintering by being heated up to 300° C. at a temperature-rising rate of 500° C./hr, retained at 500° C. for 4 hours, then heated up to 1,300° C. at a temperature-rising rate of 300° C./hr, and retained at 1,300° C. for one hour (FIG. 5).

The sintered product prepared in Example 2 showed the concentration of TOC of 3.5 mg/L and electric conductivity of 4.3 mS/m. Said product had communicated pores with a pore size of about 0.5 mm and a porosity of about 80%, being sufficiently durable with a practical strength. The X-ray analysis showed that the product had the same crystal structure of hydroxyappatite as that of the starting material.

Example 3

Figure 6:
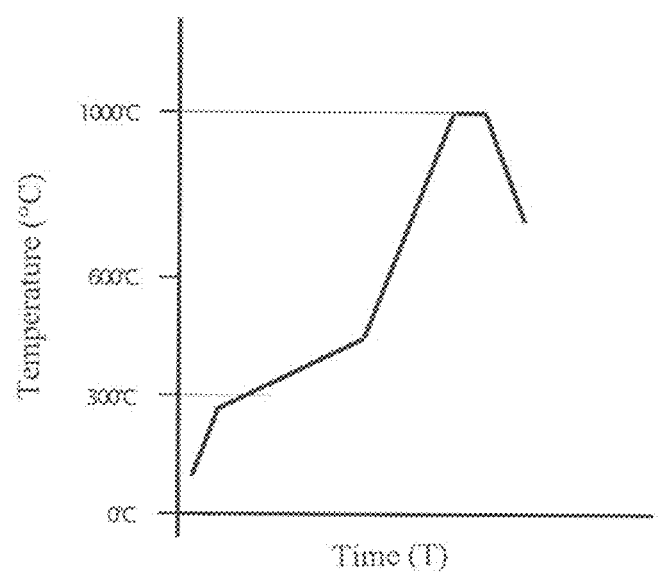
FIG. 6 is the heating and calcining (sintering) pattern according to Example 3. A vertical axis shows a calcining temperature (° C.) in a furnace and an abscissa axis shows time (hour).
Figure 7A:
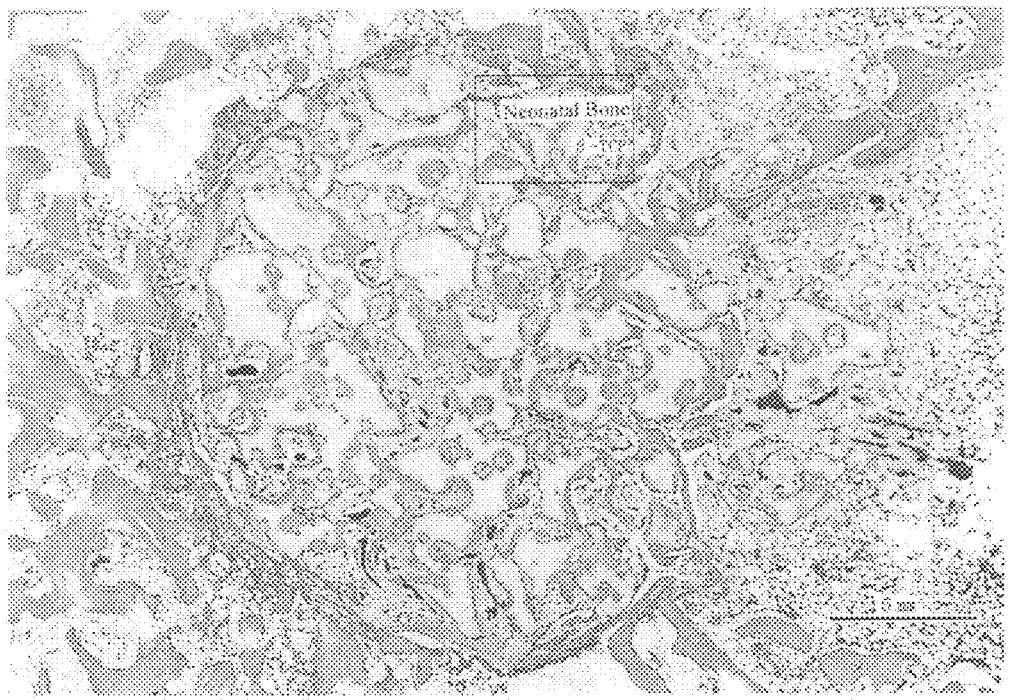
FIG. 7A is a photo (×40) of the tissue taken 4 weeks after the transplantation of granules of the calcium phosphate porous material produced in Example 1 into rabbit thighbone.
Figure 7B:
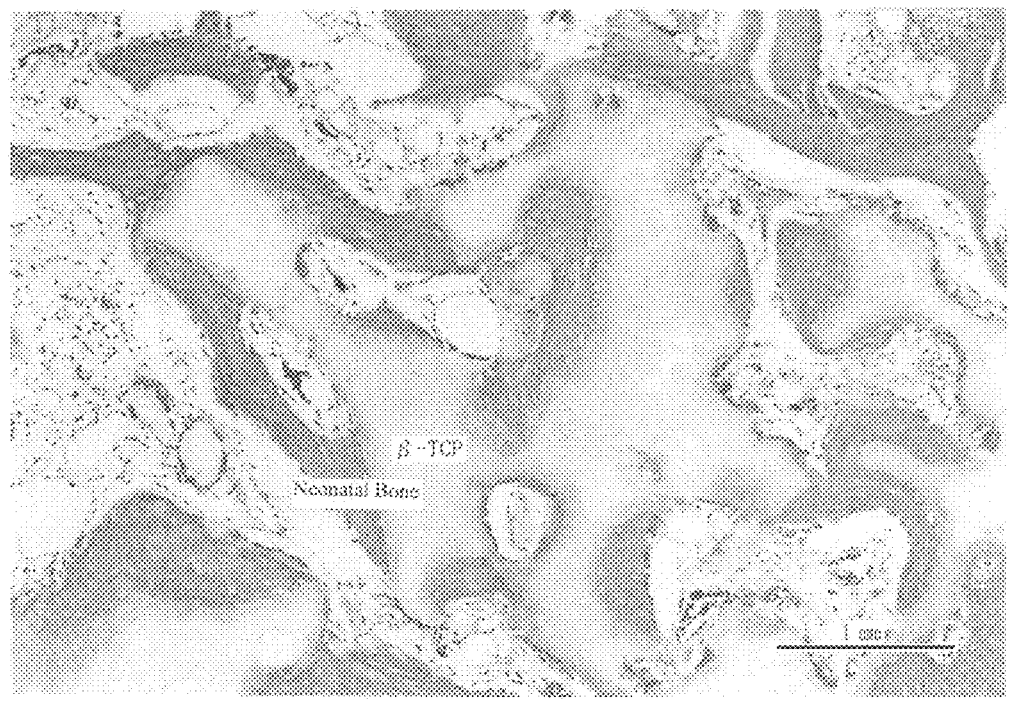
FIG. 7B is an enlarged photo of the rectangular area in the upper one (×25).
Figure 8A:
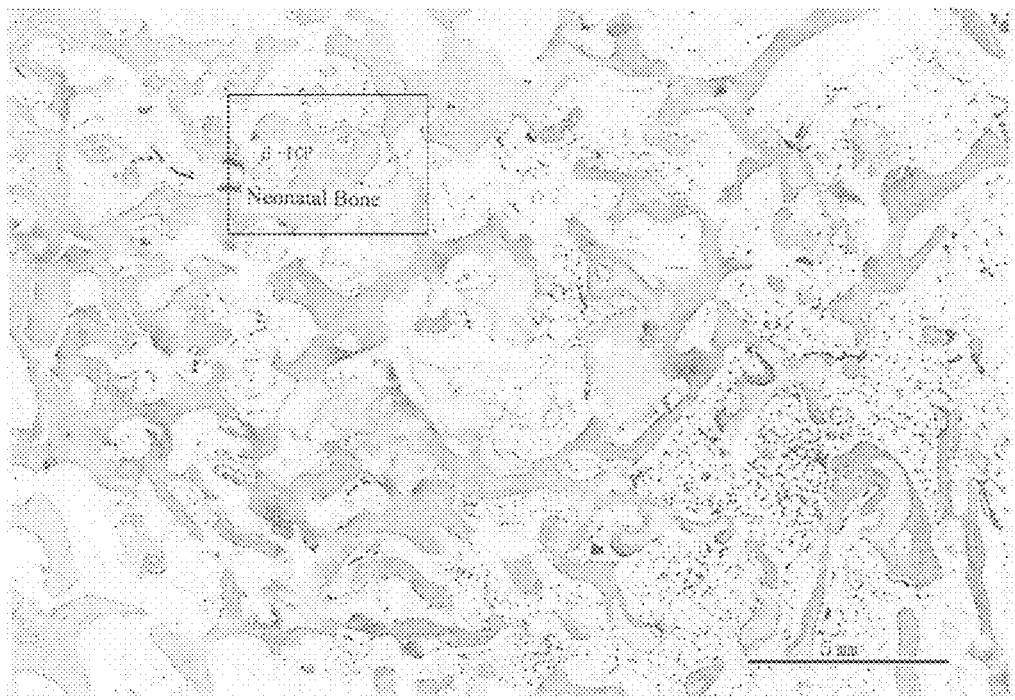
FIG. 8A is a photo (×40) of the tissue taken 12 weeks after the transplantation of granules of the calcium phosphate porous material produced in Example 1 into rabbit thighbone.
Figure 8B:
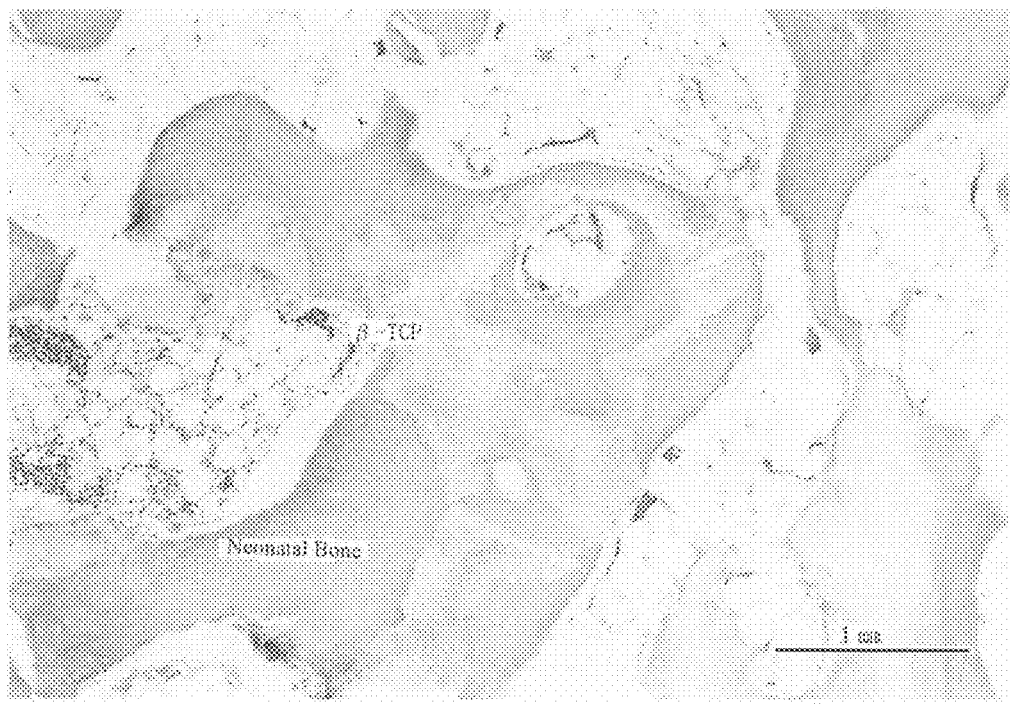
FIG. 8B is an enlarged photo of the rectangular area in the upper one (×25).
Figure 9A:
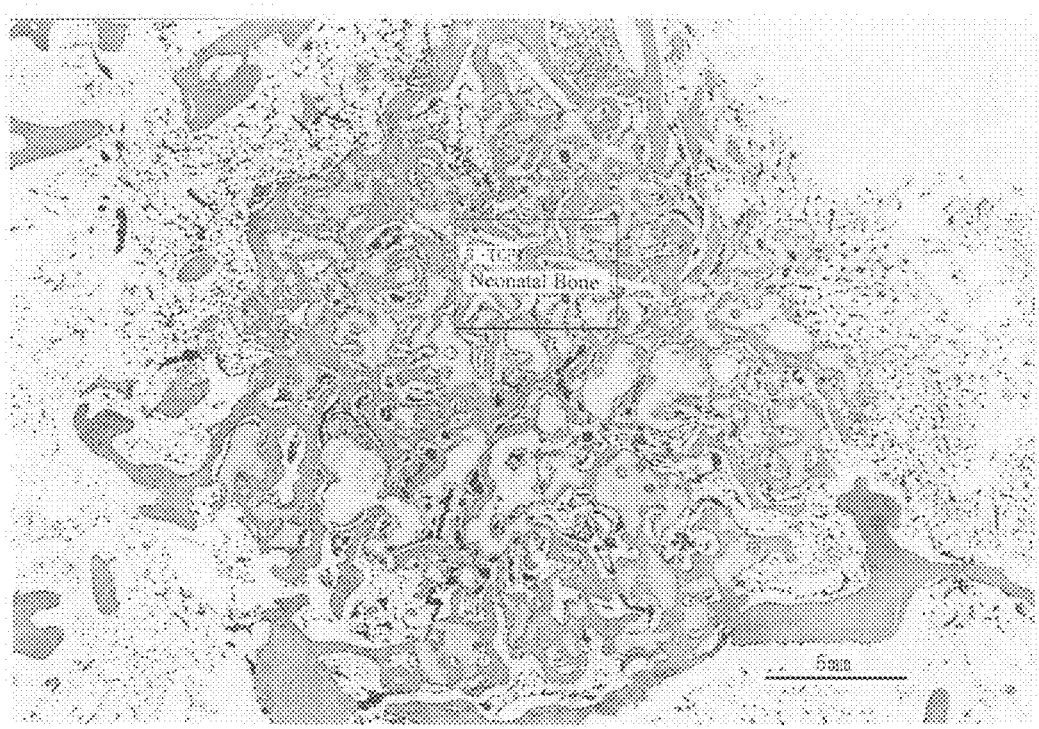
FIG. 9A is a photo (×40) of the tissue taken 4 weeks after the transplantation of granules of the calcium phosphate porous material of the prior art having the concentration of the TOC of about 30 mg/L into rabbit thighbone.
Figure 9B:
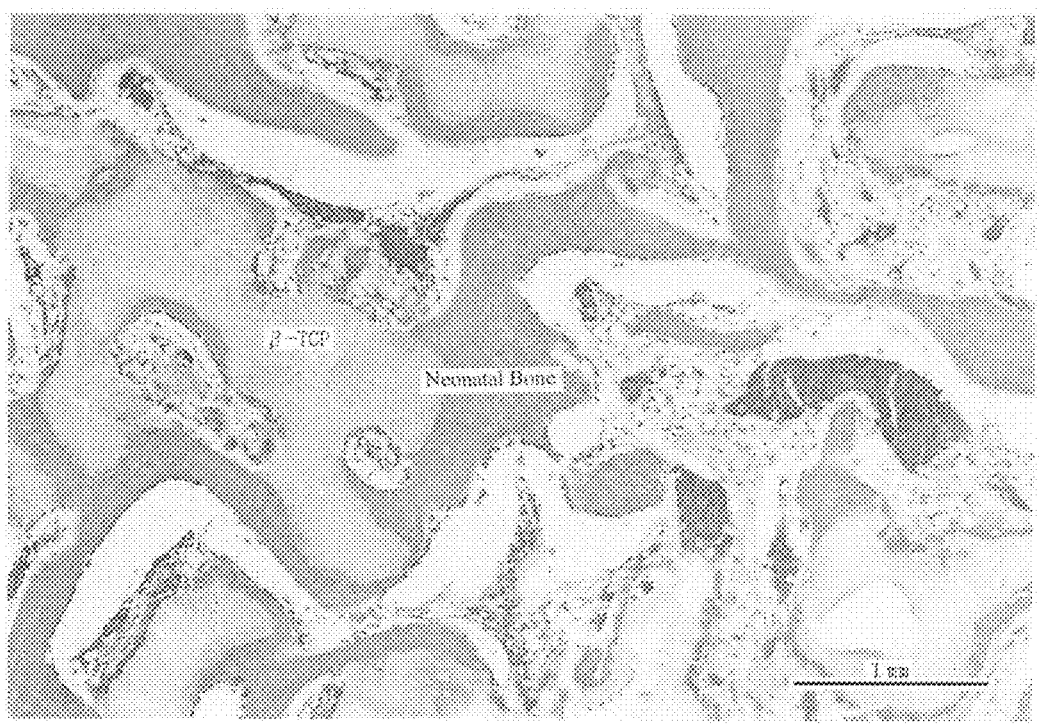
FIG. 9B is an enlarged photo of the rectangular area in the upper one (×25).
Figure 10A:
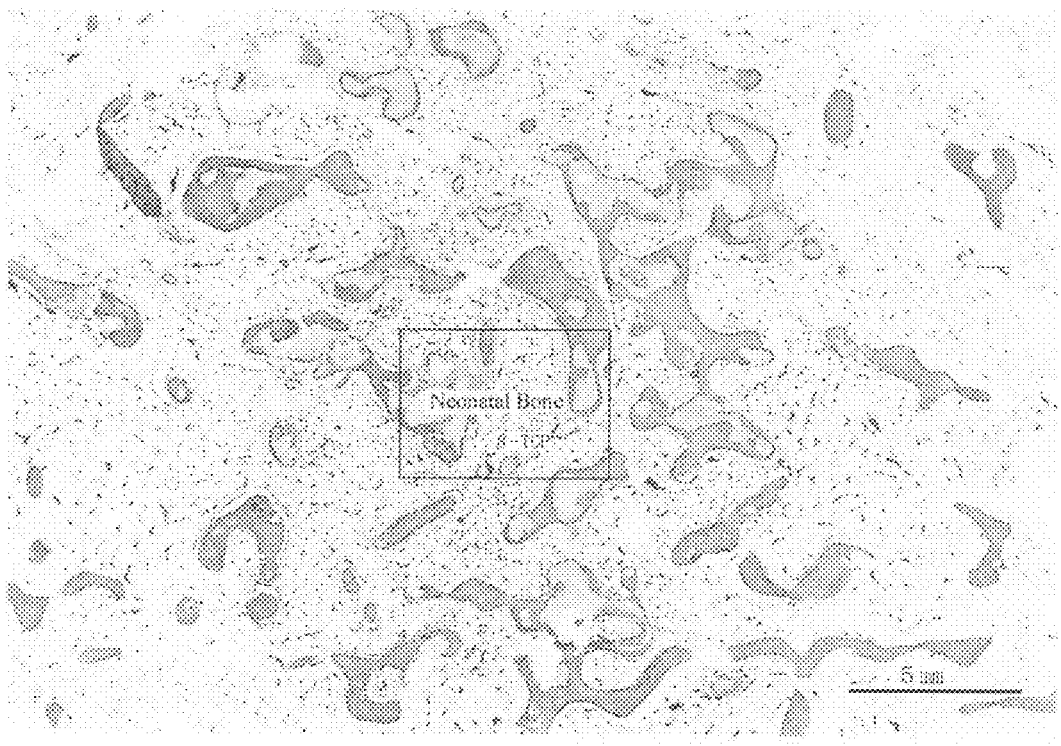
FIG. 10A is a photo (×40) of the tissue taken 12 weeks after the transplantation of granules of the calcium phosphate porous material of the prior art having the concentration of the TOC of about 30 mg/L into rabbit thighbone.
Figure 10B:
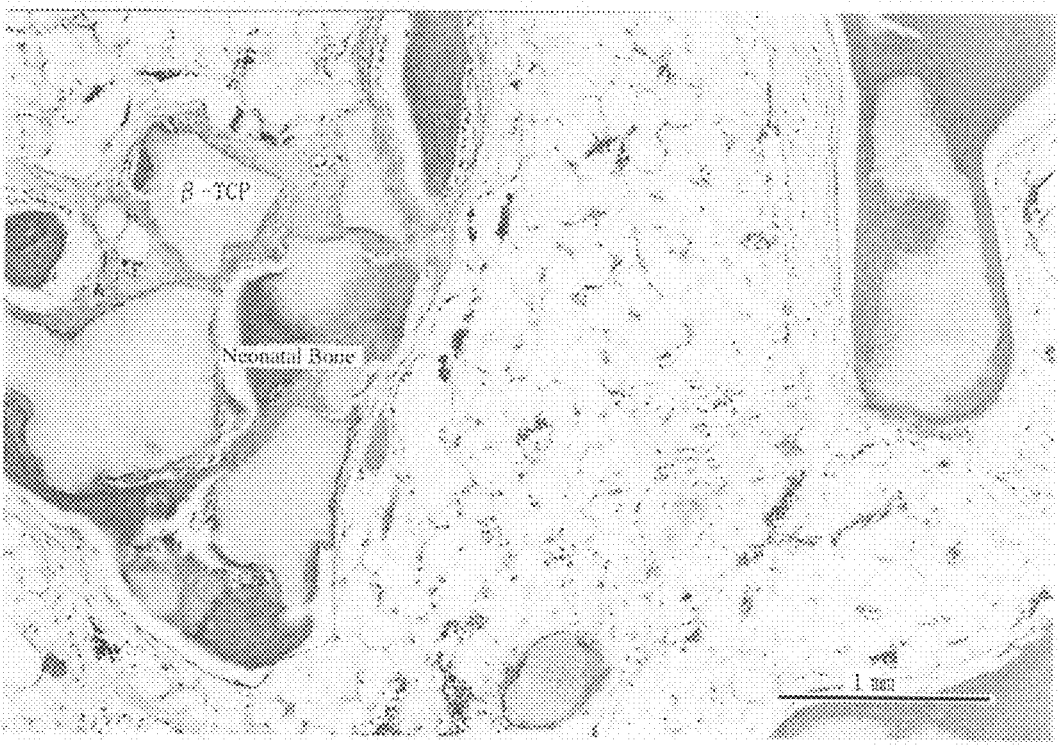
FIG. 10B is an enlarged photo of the rectangular area in the upper one (×25).

The same steps were carried out as in Example 1 except that the material was heated from a room temperature to 250° C. at a temperature-rising rate of 300° C./hr, from 250° C. to 550° C. at a temperature-rising rate of 100° C./hr, and then heated from 550° C. up to 1,000° C. at a temperature-rising rate of 300° C./hr again, and retained at 1,000° C. for 40 min (FIG. 6).

The sintered product prepared in Example 3 showed the concentration of TOC of 4.9 mg/L and electric conductivity of 4.1 mS/m. Said product had communicated pores with a pore size of about 0.2-0.8 mm. The X-ray analysis showed that the product had the same crystal structure of β-tricalcium phosphate as that of the starting material.

Example 4

The same steps were carried out as in Example 1 except that the material was heated from a room temperature to 250°

C. at a temperature-rising rate of 300° C./hr, from 250° C. to 400° C. at a temperature-rising rate of 50° C./hr, and then heated from 400° C. up to 1,000° C. at a temperature-rising rate of 300° C./hr again, and retained at 1,000° C. for 40 min.

The sintered product prepared in Example 4 showed the concentration of TOC of 1.9 mg/L and electric conductivity of 5.15 mS/m. Said product had communicated pores with a pore size of about 0.2-0.8 mm. The X-ray analysis showed that the product had the same crystal structure of β-tricalcium phosphate as that of the starting material.

Example 5

The calcium phosphate porous material made of β-tricalcium phosphate, which was prepared in Example 1, was granulated and transplanted into rabbit thighbone to examine osteogenesis. The product prepared in the prior method was used in the same procedures as a control.

The rabbits were put away for 4 and 12 weeks after the transplantation of the materials, histological evaluation was done with HE staining according to the conventional manner. It was confirmed that the calcium phosphate porous material according to the present invention had developed osteogenesis more effectively or advantageously than the control, as shown in FIGS. 7-10 wherein neonatal bone and β-TCP are indicated.

Industrial Applicability

The calcium phosphate porous material according to the present invention may be advantageously utilized in a variety of fields and applications for such as the artificial bone; prosthetic bone material; carrier for fixed enzymes used for separation, purification and adsorption of biochemical substance; filler or substituting agent for bone; and carrier for cell culture.

What is claimed is:

1. A calcium phosphate porous material made of β-tricalcium phosphate,
   wherein said porous material has a concentration of total organic carbon of 5 mg/L or less,
   wherein said porous material is produced by calcining a mixture of micronized β-tricalcium phosphate, a deflocculant and a foaming agent in a furnace,
   wherein during calcination said mixture is retained at a temperature range of 300-500° C. for 2-4 hours so that pores are produced in the porous material at said temperature range when the deflocculant and the foaming agent are decomposed and vanished,
   wherein when the mixture is retained at a temperature between 300-500° C., the mixture is exposed to a temperature-rising rate having a slope that is one third or less than a temperature-rising rate slope before and after a period of time when the mixture is retained at a temperature between 300-500° C., and
   wherein the mixture is heated to about 1000° C. after being retained at a temperature between 300-500° C.

2. The calcium phosphate porous material of claim 1, wherein said porous material has a concentration of total organic carbon of 4.5 mg/L or less.

3. The calcium phosphate porous material of claim 1, wherein said porous material has a concentration of total organic carbon of 1.9 mg/L or less.

4. An artificial bone or prosthetic bone material comprising the calcium phosphate porous material of claim 1.

5. The calcium phosphate porous material of claim 1, wherein said porous material comprises macro pores with a diameter of 100-400 μm.

6. The calcium phosphate porous material of claim 1, wherein said porous material has a porosity of about 75%.

* * * * *